United States Patent [19]

Kasdan

[11] Patent Number: 5,268,966
[45] Date of Patent: Dec. 7, 1993

[54] METHOD OF DIFFERENTIATING PARTICLES BASED UPON A DYNAMICALLY CHANGING THRESHOLD

[75] Inventor: Harvey L. Kasdan, Van Nuys, Calif.

[73] Assignee: International Remote Imaging Systems, Inc., Chatsworth, Calif.

[21] Appl. No.: 769,341

[22] Filed: Oct. 1, 1991

Related U.S. Application Data

[63] Continuation of Ser. No. 392,057, Aug. 10, 1989, abandoned.

[51] Int. Cl.$^5$ .......................................... G01N 33/48
[52] U.S. Cl. ................................... 382/6; 382/17
[58] Field of Search .................. 382/1, 6, 17

[56] References Cited

U.S. PATENT DOCUMENTS

| | | | |
|---|---|---|---|
| 4,097,845 | 6/1978 | Bacus | 382/6 |
| 4,199,748 | 4/1980 | Bacus | 382/6 |
| 4,338,024 | 7/1982 | Bolz et al. | 382/6 |
| 4,661,913 | 4/1987 | Wu et al. | 382/6 |
| 4,665,553 | 5/1987 | Gershman et al. | 382/6 |

Primary Examiner—David K. Moore
Attorney, Agent, or Firm—Limbach & Limbach

[57] ABSTRACT

A method of identifying a plurality of different types of particles in the field of view is disclosed. A first parameter is measured for each of the plurality of different particles. One of the type of particles is identified based upon the first parameter measured. Once the one type of particle is identified, a second parameter, different from the first parameter, is then measured for the one type of particle. The other types of particles in the field of view can be identified based upon the second parameter associated with the one type of particle which has been identified. In one example, color is first used to differentiate various different particles in the field of view and to identify one particular type of particle. Thereafter, a morphological parameter, such as size, associated with the one type of particle identified is measured. The measured morphological character associated with the one type of particle identified is used as a threshold to differentiate other particles in the field of view based upon the second morphological parameter. Similarly, a morphological characteristic can first be used to differentiate one type of particle. A second spectral parameter, such as color, can be measured for the one type of identified particle and can be used to differentiate other particles.

8 Claims, 2 Drawing Sheets

METHOD OF DIFFERENTIATING PARTICLES BASED UPON A DYNAMICALLY CHANGING THRESHOLD

This is a continuation of co-pending application Ser. No. 07/392,057 filed on Aug. 10, 1989 and now abandoned.

TECHNICAL FIELD

The present invention relates to a method of differentiating particles from a plurality of particles, based upon a threshold which is dynamically changing. More particularly, the present invention relates to a method of differentiating particles wherein the threshold to differentiate the particles is determined by a measurement using yet another parameter.

BACKGROUND OF THE INVENTION

Methods to identify different particles in a field of view are well-known in the art. See, for example, U.S. Pat. No. 4,175,860. Typically, the particles that are under examination are biological particles, and it is desired to automatically identify the different particles under examination.

One of the problems faced by the prior art is that various parameters (such as color) associated with each particle can vary from one sample to another sample. This variation can be caused, for example, by different stains used in the preparation of different samples or, by the age of the samples. Thus, the same type of particle appearing in different images of view may exhibit different parameters.

One solution that has been offered by the prior art is to add a normalizing substance which has a predetermined, a priori detection level. Thus, for example, calibrator particles, as disclosed in U.S. Pat. No. 4,338,024 can be added to a sample. Based upon the a priori knowledge of the color of the beads, if the color of the particle under examination exceeds that threshold, then that particle is identified as of a particular type. Clearly, such a normalizing substance is inadequate because the parameter of the particle can vary from sample to sample (due to the factors of different stain and aging as discussed above), whereas the parameter of the normalizing substance does not.

In another example of the prior art solution, the DNA of all the cells are measured. A normalizing value which is manually selected for the particular sample lot for that experiment is selected and that threshold is then used to identify the particles whose DNA exceeds that threshold or is below the threshold. With this approach, while the threshold can vary, it requires manual interpretation and intervention to determine the particular threshold adequate for each of these experiments.

SUMMARY OF THE INVENTION

In the present invention, a method of identifying a plurality of different particles in a field of view is disclosed. The method comprises the steps of measuring a first parameter for each one of the plurality of different particles. One of the particles is identified based upon the first parameter measured for the one particle. A second parameter, different from the first parameter associated with the one particle, is then measured for the one particle identified. The other particles in the field of view are identified based upon the second parameter associated with the one particle that has been identified.

DETAILED DESCRIPTION OF THE DRAWINGS

Figure 1:
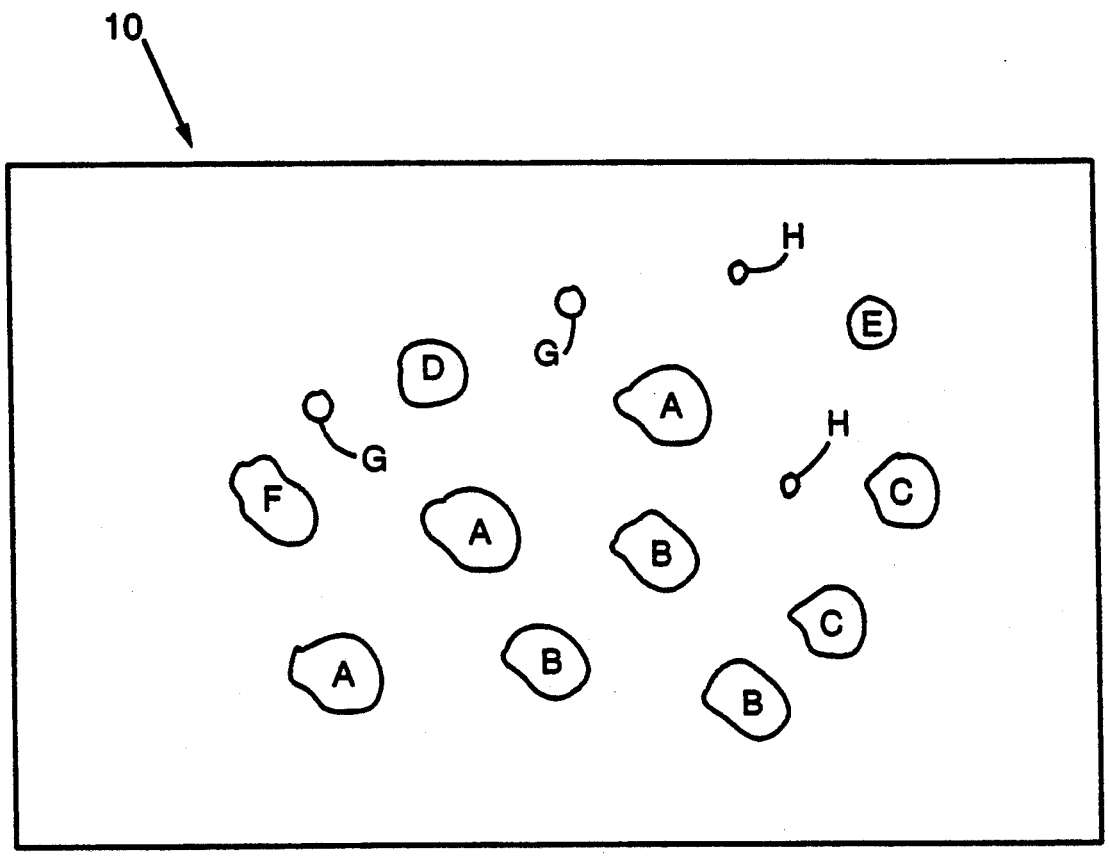
FIG. 1 is a schematic d of an image of a view with a plurality of different types of particles shown.
Figure 2:
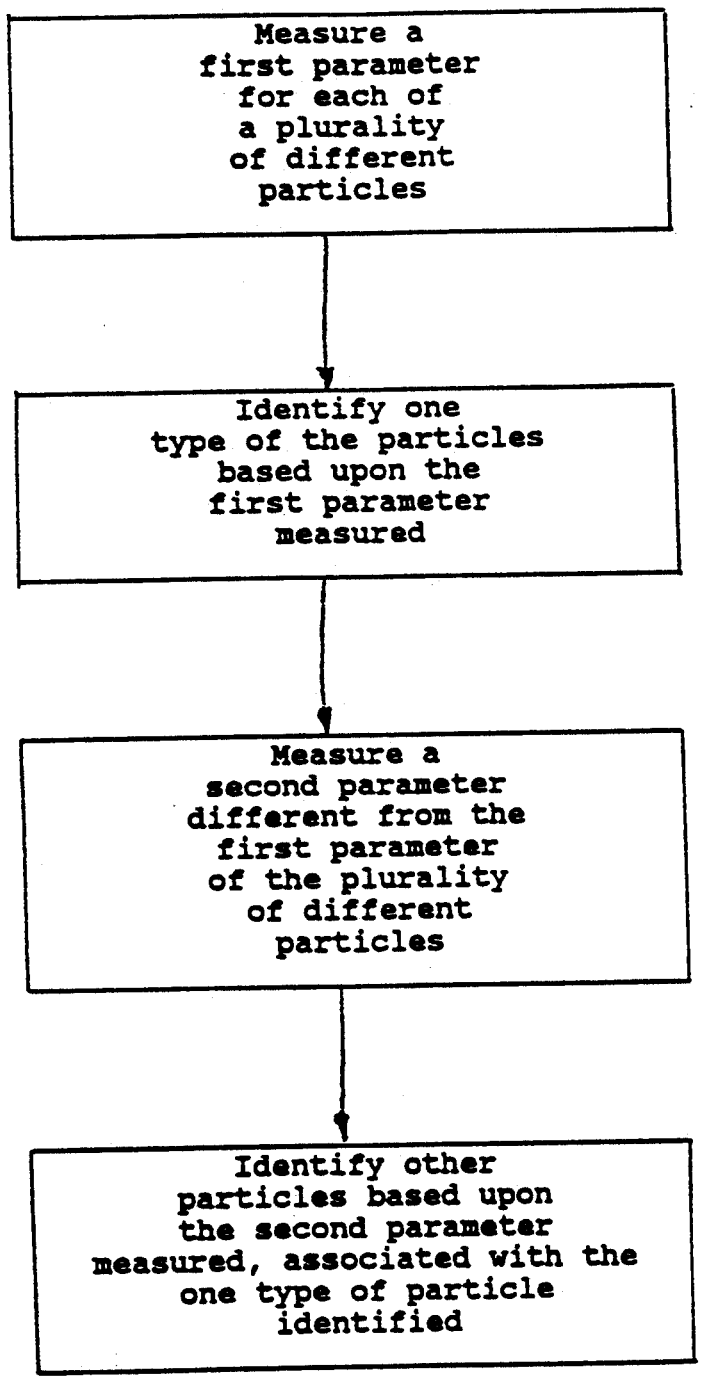
FIG. 2 is a flow chart of the method of the present invention.

Referring to FIG. 1, there is shown an image 10 of a plurality of particles in a field of view. Although the method of the present invention will be described with respect to biological particles in a field of view, it can be appreciated that the method of the present invention can be practiced with any type of particles or with any type of members in a group of members.

As shown in FIG. 1, a plurality of different types of particles (A ... H) are shown in the image 10. Thus, there are three particles of type A, three particles of type B, two particles of type C ... and two particles of type H. However, when an image 10 of a plurality of particles is presented, the type of particles is not a priori known. Further, statistical variations in certain parameters of a type of particle may exist. For example, a type A particle may be "larger" in size than the particles of type B and type C. However, not all particles of Type A may be of the same size. The method of the present invention distinguishes the type of particles and identifies them in the image 10 in the field of view.

As used herein, the term "identify" means to determine the label or identifier which is attached to a particular particle or group of particles. Further the term also includes the characteristics, e.g. statistical variations, of the identified group of particles. The term "distinguish" or "differentiate" means to separate a group of particles into two or more subpopulation groups based upon one or more parameters. The separation, however, does not necessarily involve identification of the subpopulation groups, i.e. determination of the label for each of the subpopulation groups.

In the method of the present invention, a first parameter is measured for each one of the plurality of particles in the image 10. The first parameter can be a parameter such as color.

Based upon the color intensity of the various particles, one of the type of particles, such as particle A, is identified. Thereafter, a second parameter, different from the first parameter, is measured for the particles which have been identified; namely, particles A. The second parameter can be a morphological parameter, such as size, which is different from spectral parameter such as color. Thus, the particles A identified are then measured for size.

Finally, the other particles in the field of view 10 are identified, based upon the second parameter. The second parameter is measured for each of the other particles. The measurement of the second parameter (for each of the other particles, other than particles identified as being of type A) is compared to the measurement of the parameter determined for the particles identified as being of type A. Based upon this comparison, the other particles are then identified. Thus, for example, the morphological characteristic of size for all the other particles is then compared to the size of particle type A, and is identified based upon this comparison. If the size of a particle exceeds that of the size for particles of type A, then the particle is identified as being of a certain type, such as type B.

It should be noted while the method has been described with regard to the first parameter, which is measured as being a spectral parameter and the second parameter as being a morphological parameter, the method of the present invention can also be used where the first parameter is a morphological parameter and wherein the second parameter is a spectral parameter.

The method of the present invention will now be described with specific reference to the following examples:

EXAMPLE 1

In a biological sample containing lymphocytes, monocytes and neutrophils, it is desired to separately identify all of these different types of particles. However, the difference between monocytes and neutrophils cannot be distinguished based upon color because they differ from sample to sample. Thus, in the method of the present invention, the size of all the different particles is first measured. Lymphocytes are then distinguished from monocytes and neutrophils by the size of the Lymphocyte particles. If the size of the particles is less than approximately 50 $\mu m^2$ (200 0.5×0.5 $\mu m$ pixel), for example, then the particles are deemed to be lymphocytes, whereas all other particles contain both monocytes (if any) and neutrophils (if any).

Thereafter, the color of the lymphocytes so identified is measured. The average color of all the lymphocytes identified is measured. The color measured for the identified lymphocytes is then used as a threshold to differentiate monocytes from neutrophils. If the color of a particular particle is greater than the average color of the lymphocytes, then the particle is a neutrophil. If the color of the particle under examination is less than the average color of the identified lymphocytes, then the particle under examination is a monocyte. In this manner, monocytes and neutrophils can be distinguished from one another and identified based upon the average color of lymphocytes in the same sample in which the monocytes and the neutrophils exist.

EXAMPLE 2

A plurality of different types of particles including basophils are shown in an image in a field of view. The basophils are identified by color from all the other types of particles by conventional means or by the use of zeroth green quantile for B021 stained cells. For a description of quantile measurement, see co-pending U.S. application Ser. No. 357,324, filed on May 25, 1989 and assigned to the same assignee as the present invention. That co-pending application is incorporated herein by reference. Thereafter, the area of the identified basophils is measured in pixels and the average area of all basophils thus identified is computed. From the average area of the measured basophils, the pixel size can be determined, assuming a nominal basophil area of about 42 $\mu m^2$. From the pixel size determined, the other particles (such as neutrophils, eosinophils and monocytes) can be distinguished based upon this pixel size by computing all particle areas and assigning all particles with areas greater than 50 $\mu m^2$ to the neutrophil, eosinophil and monocyte category. Alternatively, this decision may be based on the area of a particle relative to the basophil average.

EXAMPLE 3

A plurality of different types of particles including known cancer cells and cells that are potentially cancerous are in the imaged field of view. The plurality of different types of particles are subjected to reaction with an antibody which has a color tag attached thereto. The antibody would attach itself to the known cancer cells. Those known cancer cells would have a particular color, depending on the color tag attached to the antibody. The colored cells are then located and the ploidy of the known cancer cells are measured. The ploidy of the subpopulation of known cancer cells would have a statistical distribution. Based upon this measured ploidy, the potentially cancerous cells are differentiated from the healthy cells. That is, the ploidy of the potentially cancerous cells and of the healthy cells are also measured. If the ploidy of a measured unknown cell is approximately on the same order (i.e. within the statistical distribution) as the ploidy of the known cancer cells, then that cell is potentially cancerous. On the other hand, if the ploidy of a measured unknown cell is far less than the ploidy (i.e. outside of the statistical distribution) of the measured known cancer cells, then the unknown cell is a healthy cell. In this manner, healthy cells can be distinguished from potentially cancerous cells.

EXAMPLE 4

A gene probe for human papilloma virus (HPV) is hybridized to a plurality of different cells. The gene probe has an enzyme label attached thereto. Upon introduction of substrate material, the substrate is converted by the enzyme and produces a local colored deposit within the cell. The ploidy of the HPV population (identified by the presence of the colored deposits) may be measured and compared to the ploidy of the non-HPV population (identified by the absence of colored deposits) to determine the degree to which the HPV population has changed from normal.

The theory of operation of the method of the present invention is as follows. The invention is of a method which determines a dynamically changeable normalization threshold from which other particles can be differentiated. Unlike the prior art where the threshold is fixed or is a priori known, the method of the present invention recognizes that the threshold for each sample would differ depending on factors such as age and color stain which vary from sample to sample. Thus, the method of the present invention overcomes the problem of experimental variability; therefore, the same method can be used to differentiate cells in different experiments where the experiments of the different samples are subject to different variables.

What is claimed is:

1. A method of identifying a plurality of different types of unknown particles in a field of view, comprising the steps of:
    a) measuring a first parameter for each of said plurality of different types of unknown particles;
    b) identifying one of said plurality of different types of unknown particles based upon the first parameter measured to produce a one type known particle;
    c) measuring a second parameter different from said first parameter, for each of said plurality of different types of unknown particles;
    d) measuring the second parameter for said one type known particle;

e) identifying another type of particle from said plurality of different types of unknown particles in said field of view based upon the second parameter measured for said one type known particle.

2. The method of claim 1, wherein said first parameter is a morphological parameter and wherein said second parameter is a spectral parameter.

3. The method of claim 1, wherein said first parameter is a spectral parameter and wherein said second parameter is a morphological parameter.

4. A method of differentiating a first type of cell in a plurality of fields of view where the first type of cell in different fields of view differ in a first detectable parameter, wherein the same method is used to differentiate the first type of cell from other unknown cells in each field of view, said method comprising the steps of:

a) selecting a field of view;
b) measuring a second parameter of each of said unknown cells in said selected field of view;
c) identifying one of said cells from said unknown cells, other than the first cell, based upon said second parameter measured;
d) measuring said first detectable parameter, different from said second parameter, associated with said cell identified in step c; and
e) differentiating said first cell from other unknown cells based upon the first parameter measured for said cell identified in step c.

5. The method of claim 4, wherein said first parameter is a morphological parameter, and wherein said second parameter is a spectral parameter.

6. The method of claim 4, wherein said first parameter is a spectral parameter, and wherein said second parameter is a morphological parameter.

7. The method of claim 4, wherein said differentiating step of e) further comprising:

measuring the first parameter of the other unknown cells in the field of view;
comparing the first parameter of each cell measured to the first parameter of said identified one cell and differentiating said first cell from said other cells based upon said comparing.

8. A method of identifying a plurality of first members from a group of members, comprising the steps of:

measuring a first characteristic of each member of said group of members;
identifying a plurality of second members from said group of members based upon said first characteristic measured;
measuring a second characteristic, different from said first characteristic, of said second members identified; and
identifying the plurality of first members based upon the second characteristic of each of said second members measured.

* * * * *